(12) United States Patent
O'Mahony et al.

(10) Patent No.: US 12,220,513 B2
(45) Date of Patent: Feb. 11, 2025

(54) PATIENT FLUID REMOVAL MAKEUP

(71) Applicant: GAMBRO LUNDIA AB, Lund (SE)

(72) Inventors: John O'Mahony, Maple Grove, MN (US); Rickie Stuva, New Hope, MN (US)

(73) Assignee: Gambro Lundia AB, Lund (SE)

( * ) Notice: Subject to any disclaimer, the term of this patent is extended or adjusted under 35 U.S.C. 154(b) by 921 days.

(21) Appl. No.: 17/055,791

(22) PCT Filed: May 7, 2019

(86) PCT No.: PCT/EP2019/061626
§ 371 (c)(1),
(2) Date: Nov. 16, 2020

(87) PCT Pub. No.: WO2019/219442
PCT Pub. Date: Nov. 21, 2019

(65) Prior Publication Data
US 2021/0196880 A1    Jul. 1, 2021

Related U.S. Application Data

(60) Provisional application No. 62/672,715, filed on May 17, 2018.

(51) Int. Cl.
*A61M 1/34* (2006.01)
*A61M 1/14* (2006.01)
(Continued)

(52) U.S. Cl.
CPC .......... *A61M 1/3607* (2014.02); *A61M 1/154* (2022.05); *A61M 1/1647* (2014.02);
(Continued)

(58) Field of Classification Search
CPC .. A61M 1/3607; A61M 1/154; A61M 1/1647; A61M 1/34; A61M 1/3403; A61M 1/3441; A61M 1/36; A61M 1/3606; A61M 1/36224; A61M 1/36225; A61M 1/3653; A61M 1/14; A61M 1/1566; A61M 1/341;
(Continued)

(56) References Cited

U.S. PATENT DOCUMENTS 5,211,849 A    5/1993  Kitaevich
10,098,993 B2 *  10/2018  Meyer ................. A61M 1/1696
(Continued)

FOREIGN PATENT DOCUMENTS

AU    2012300546    3/2014
EP    2939156    11/2015
(Continued)

OTHER PUBLICATIONS

Office Action issued in Japan for Application No. 2020-564367 dated Feb. 27, 2023 (5 pages).
(Continued)

*Primary Examiner* — Fred Prince
(74) *Attorney, Agent, or Firm* — Mueting Raasch Group (57) ABSTRACT

A patient fluid removal compensation volume may be determined to make up for the patient fluid removal that does not occur during machine down times, and the patient fluid removal rate may be increased until the compensating volume is satisfied.

39 Claims, 5 Drawing Sheets

(51) Int. Cl.
  *A61M 1/16* (2006.01)
  *A61M 1/18* (2006.01)
  *A61M 1/36* (2006.01)

(52) U.S. Cl.
  CPC ............ *A61M 1/34* (2013.01); *A61M 1/3403* (2014.02); *A61M 1/3441* (2013.01); *A61M 1/36* (2013.01); *A61M 1/3606* (2014.02); *A61M 1/36224* (2022.05); *A61M 1/36225* (2022.05); *A61M 1/3653* (2013.01); *A61M 1/14* (2013.01); *A61M 1/1566* (2022.05); *A61M 1/341* (2014.02); *A61M 2205/18* (2013.01); *A61M 2205/3334* (2013.01); *A61M 2205/3393* (2013.01)

(58) Field of Classification Search
  CPC ...... A61M 2205/18; A61M 2205/3334; A61M 2205/3393
  USPC ......................................... 210/645, 646, 647
  See application file for complete search history.

(56) References Cited

U.S. PATENT DOCUMENTS

| | | |
|---|---|---|
| 2008/0154170 A1 | 6/2008 | Lannoy |
| 2008/0221498 A1* | 9/2008 | Ogihara ............... A61M 1/3603 604/6.14 |
| 2011/0017667 A1 | 1/2011 | Delmage |
| 2012/0273354 A1 | 11/2012 | Orhan |
| 2013/0213890 A1 | 8/2013 | Kelly |
| 2013/0274642 A1 | 10/2013 | Soykan |
| 2015/0034557 A1 | 2/2015 | Pouchoulin |
| 2015/0060362 A1 | 3/2015 | Pouchoulin |
| 2017/0189602 A1* | 7/2017 | Thys ................... A61M 1/3644 |

FOREIGN PATENT DOCUMENTS

| | | |
|---|---|---|
| EP | 3015123 | 5/2016 |
| EP | 3290069 | 2/2018 |
| WO | WO 2013/019994 | 2/2013 |
| WO | WO 2013/144793 | 10/2013 |
| WO | WO 2015/183981 A2 * | 12/2015 |

OTHER PUBLICATIONS

PCT International Search Report and Written Opinion for PCT/EP2019/061626 dated Jul. 18, 2019 (11 pages).

Swedish Search Report for Application No. 1850662-6 dated Oct. 29, 2019 (9 pages).

* cited by examiner

PATIENT FLUID REMOVAL MAKEUP

This application is a U.S. National Stage Application of International Application No. PCT/EP2019/061626, filed 7 May 2019 and published in English on 21 Nov. 2019 as International Publication No. WO 2019/219442 A1, which claims the benefit of U.S. Provisional Application No. 62/672,715, filed 17 May 2018, the disclosures of which are incorporated by reference herein in their entirety.

The disclosure herein relates to extracorporeal blood treatment. More particularly, the disclosure relates to systems and methods including patient fluid removal makeup.

Extracorporeal blood treatment may refer to taking blood from a patient, treating the blood outside the patient, and returning the treated blood to the patient. Extracorporeal blood treatment is typically used to extract undesirable matter or molecules from the patient's blood, and/or to add beneficial matter or molecules to the blood. Extracorporeal blood treatment may be used with patients incapable of effectively eliminating matter from their blood, for example, in the case of a patient who is suffering from temporary or permanent kidney failure. These and other patients may, for instance, undergo extracorporeal blood treatment to add to or to eliminate matter from their blood, to maintain an acid-base balance or to eliminate excess body fluids.

In a variety of extracorporeal blood treatments, one or more fluids, or liquids, may be supplied to the extracorporeal blood treatment apparatus for use during the treatments and one or more fluids may be collected as a part of the treatments. Both the supplied and collected fluids may be stored in one or more reservoirs. These reservoirs may, during the course of treatment of a single patient, need to be replaced as they are either emptied (in the case of fluids supplied as a part of the treatment) or are filled to capacity (in the case of fluids collected as a part of the treatment).

During the course of an extracorporeal blood treatment, various issues may occur that result in stoppage of one or more pumps of the extracorporeal blood treatment system. In turn, no, or little, amount of patient fluid may be removed during the stoppage. For example, an effluent bag change may result in stoppage of an effluent pump and a dialysate pump (as well as the remainder of the dialysate circuit), and during the effluent bag change, no fluid may be removed.

SUMMARY

The present disclosure describes systems and methods that may be described as providing patient fluid removal (PFR) makeup. The PFR makeup may "make up" for lost PFR during stoppages of one or more pumps such as the effluent pump and dialysate pump due to, e.g., voluntary actions by a user such as a reservoir change. Generally, in one embodiment, the illustrative systems and methods may use, or utilize, a PFR makeup volume that may serve as a "tally" of fluid removal that is lost, or does not occur, during the stoppages. An increase in PFR rate may be used to compensate for the fluid removal that was lost during the stoppages, and the increased PFR rate may be utilized until the PFR makeup volume is "made up."

PFR makeup may be described as an additional effluent flow rate that is calculated to compensate for PFR volume lost (i.e., not removed) when treatment is stopped due to an alarm or fluid bag change. The PFR volume lost may not be calculated based on weight, or mass, of an effluent reservoir, and instead, may be based on the prescribed PFR volume and the time of the stoppage of the treatment. For example, during continuous renal replacement therapy (CRRT) treatments, the effluent flow rate may be increased to make up for treatment "down times" of up to 10 minutes due to bag changes and/or pump stoppage due to faults. This may be an operator selectable option called "PFR makeup" (e.g., selectable using a graphical user interface) and may allow the actual commanded PFR volume over the treatment time to match the prescription PFR volume.

One illustrative extracorporeal blood treatment system may include extracorporeal blood treatment apparatus and a computing apparatus including one or more processors and operatively coupled to the extracorporeal blood treatment apparatus. The extracorporeal blood treatment apparatus may include one or more pumps and one or more sensors for use in performing an extracorporeal blood treatment, and the one or more pumps may include an effluent pump to remove fluid from a patient during extracorporeal blood treatment according to a patient fluid removal rate. The computing apparatus may be configured to determine a patient fluid removal makeup volume in response to stoppage of the effluent pump. The patient fluid removal makeup volume may be a volume of patient fluid removal that did not occur during the stoppage. The computing apparatus may be further configured to increase the patient fluid removal rate in response to stoppage of the effluent pump for use after the stoppage ceases.

One illustrative method for an extracorporeal blood treatment system may include providing extracorporeal blood treatment apparatus including at least one or more pumps and one or more sensors. The one or more pumps may include an effluent pump to remove fluid from a patient during extracorporeal blood treatment according to a patient fluid removal rate. The illustrative method may further include determining a patient fluid removal makeup volume in response to stoppage of the effluent pump. The patient fluid removal makeup volume may be a volume of patient fluid removal that did not occur during the stoppage. The illustrative method may further include increasing the patient fluid removal rate in response to stoppage of the effluent pump for use after the stoppage ceases.

In one or more embodiments, the computing apparatus may be further configured to execute or the method may further include limiting the patient fluid removal makeup volume to less than or equal to a patient fluid removal makeup volume limit. Further, in one or more embodiments, the patient fluid removal makeup volume limit may be equal to a patient fluid removal rate times a selected period of time.

In one or more embodiments, increasing the patient fluid removal rate may include increasing the patient fluid removal rate by a selected percentage in response to an increased patient fluid removal makeup volume. For example, the selected percentage may be 20%.

In one or more embodiments, increasing the patient fluid removal rate may include increasing the patient fluid removal rate by a selected rate of fluid removal related to mass of the patient in response to an increased patient fluid removal makeup volume. For example, the selected rate of fluid removal may be 2 milliliters per hour per kilogram.

In one or more embodiments, the stoppage of the effluent pump may include one or more of a bag change, an alarm condition, and a user-initiated action. In one or more embodiments, the computing apparatus may be further configured to execute or the method may further include decreasing the patient fluid removal makeup volume in response to continuation of the effluent pump when using the increased patient fluid removal rate.

In one or more embodiments, the computing apparatus may be further configured to execute or the method may further include decreasing the patient fluid removal rate in response to an additional volume of fluid removed from the patient is equal to the patient fluid removal makeup volume. Further, for example, decreasing the patient fluid removal rate may include returning the patient fluid removal rate to the value prior to the increase thereto.

In one or more embodiments, the computing apparatus may be further configured to execute or the method may further include allowing a user select whether to enable the patient fluid removal makeup volume is to be increased. In one or more embodiments, the computing apparatus may be further configured to execute or the method may further include providing continuous renal replacement therapy (CRRT).

The above summary of the present disclosure is not intended to describe each embodiment or every implementation thereof. Advantages, together with a more complete understanding of the present disclosure, will become apparent and appreciated by referring to the following detailed description and claims taken in conjunction with the accompanying drawings.

DETAILED DESCRIPTION OF ILLUSTRATIVE EMBODIMENTS

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems and methods including patient fluid removal (PFR) makeup for use in extracorporeal blood treatments shall be described with reference to FIGS. 1-7. It will be apparent to one skilled in the art that elements or processes from one embodiment may be used in combination with elements or processes of the other embodiments, and that the possible embodiments of such systems and methods using combinations of features set forth herein is not limited to the specific embodiments shown in the Figures and/or described herein. Further, it will be recognized that the embodiments described herein may include many elements that are not necessarily shown to scale. Still further, it will be recognized that timing and use of the processes described herein may be modified but still fall within the scope of the present disclosure, although certain timings of or use of certain processes may be advantageous over others.

The present disclosure may be described as systems and methods including patient fluid removal (PFR) makeup for extracorporeal blood treatment such as, e.g., continuous renal replacement therapy (CRRT). The illustrative PFR makeup processes may compensate for PFR volume lost when a treatment is stopped due to, e.g., a fault, an alarm, or a fluid bag change. The illustrative PFR makeup processes may temporarily increase a PFR rate when treatment resumes to make the average commanded PFR rate match the prescribed PFR rate.

For example, each time the effluent pump (and, e.g., the dialysate pump) is stopped, the patient is not getting the prescribed fluid removal rate. Part of this PFR rate is to compensate for additional fluid gain from external sources and the patient will be gaining fluid during fluid pump stoppages. If the accumulated down time is less than 10 minutes, then the illustrative systems and methods may increase the PFR rate for a short period upon restarting fluid removal to automatically compensate for the accumulated PFR error during stoppages due to, e.g., alarms or bag changes. This makeup flow may be limited based on the user defined PFR rate and as a function of the patient body weight to prevent hypotension.

The illustrative systems and methods may be described as being able to maintain the patient fluid balance. For instance, in intensive care units (ICU), multiple pumps may be infusing medications simultaneously into the patient, and the net fluid gain has to be counterbalanced with PFR to maintain the patient fluid balance. The illustrative patient fluid makeup processes described herein may reduce the work load for nurses by eliminating the action of manually compensating for PFR errors as a result of bag changes and alarms. The illustrative patient fluid makeup processes may be optional and selectable by a user. For example, a graphical user interface may allow a user to enable or disable the patient fluid makeup processes.

In one or more embodiments, if the fluid pumps (e.g., effluent pump, dialysate pump, etc.) are stopped for a period of time less than 10 minutes (for example, due to voluntary user action such as a bag change or due to an alarm condition), when the fluid pumps start to run again, the illustrative systems and methods may compensate for the lost PFR due to the stopped fluid pumps. Further, cumulative PFR makeup volume may be limited to a selected value such as, e.g., 10 minutes at the current PFR setting. If PFR makeup is enabled, the illustrative PFR makeup processes may maintain a volume (e.g., in milliliters (ml)) of how much PFR makeup is to be performed. For example, each time the effluent pump is stopped, the current PFR makeup volume increases (e.g., subject to a maximum PFR makeup volume) by the following volume: PFR makeup volume increase=the duration of effluent pump stoppage time multiplied by the PFR rate setting.

The maximum PFR makeup volume may be limited to about 10 minutes at the current PFR setting. If the PFR setting is changed by the user, the above max shall be recalculated, which may mean that the maximum PFR volume can be reduced down to zero if PFR is set to zero. Any previous PFR makeup value greater than the new maximum would not be replaced. When the maximum is reached, the illustrative patient fluid makeup processes may declare a corresponding event. When the effluent pump is running, the commanded effluent pump speed may increase, and the current makeup volume may decrease at a rate of either 20% of the current PFR rate or 2 ml/hour/kilogram (kg) multiplied by the patient's weight in kg, whichever is less until current makeup volume is reduced to zero. The weight-based flow limitation may be described as providing additional follow-up on the PFR makeup flow when high PFR rates are used on small patients due to nurses compensating for additional infusion of fluids.

Figure 1:
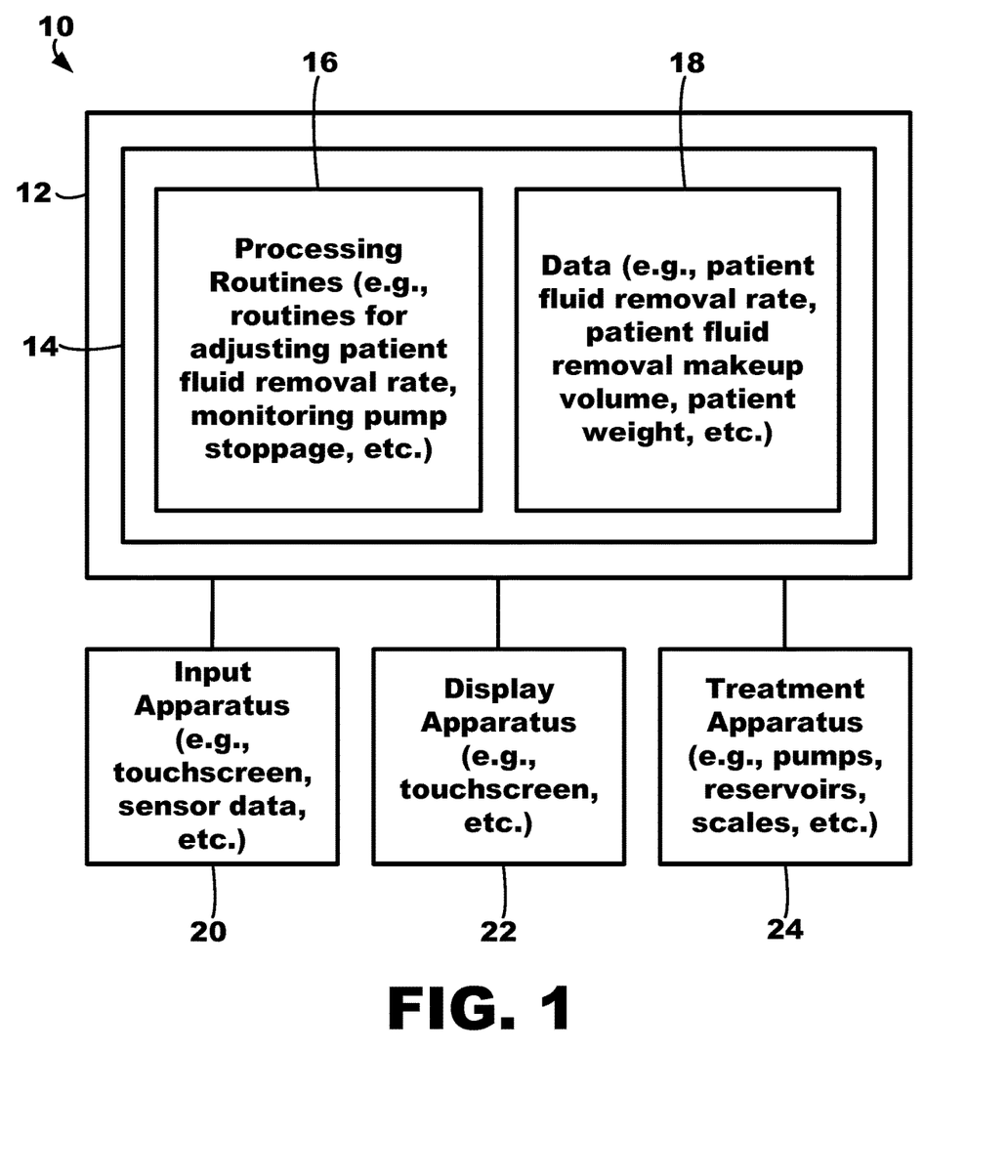
FIG. 1 is a block diagram of an illustrative extracorporeal blood treatment system including input apparatus, display apparatus, and treatment apparatus that may utilize the methods and processes described herein.

An exemplary extracorporeal blood treatment system 10 depicted in FIG. 1 may be used to execute, or perform, the exemplary methods and/or processes described herein. In at least one embodiment, the system 10 may be a machine for the extracorporeal treatment of blood. The system 10 could, for example, alternatively be a blood processing device or a blood component preparation device or other medical apparatus for fluid delivery/collection.

As shown, the exemplary extracorporeal blood treatment system 10 includes computing apparatus 12. The computing apparatus 12 may be configured to receive input from input apparatus 20 and transmit output to display apparatus 22. Further, the computing apparatus 12 may include data storage 14. Data storage 14 may allow for access to processing programs or routines 16 and one or more other types of data 18 that may be employed to carry out exemplary methods and/or processes (e.g., running pumps, computing PFR makeup volume, increasing or decreasing PFR rate, running a treatment, calculating a maximum PFR makeup volume, determining problems with a treatment, exchanging/changing reservoirs, notifying operators/users of problems, displaying status information, etc.) for use in performing extracorporeal blood treatments. For example, the computing apparatus 12 may be configured to calculate a PFR makeup volume based on stoppages of one or more pumps and increase PFR rate based on the stoppages and/or the PFR makeup volume (e.g., which will be described further herein with respect to FIGS. 3-7).

The computing apparatus 12 may be operatively coupled to the input apparatus 20 and the display apparatus 22 to, e.g., transmit data to and from each of the input apparatus 20 and the display apparatus 22. For example, the computing apparatus 12 may be electrically coupled to each of the input apparatus 20 and the display apparatus 22 using, e.g., analog electrical connections, digital electrical connections, wireless connections, bus-based connections, etc. As described further herein, an operator may provide input to the input apparatus 20 to manipulate, or modify, one or more graphical depictions displayed on the display apparatus 22 to select and view various information such as, for example, enabling or disabling PFR makeup processes and functionality as described herein.

Further, various devices and apparatus may be operatively coupled to the computing apparatus 12 to be used with the computing apparatus 12 to perform one or more extracorporeal procedures/treatments as well as the functionality, methods, and/or logic described herein. As shown, the system 10 may include input apparatus 20, display apparatus 22, and treatment apparatus 24 operatively coupled to the computing apparatus 12 (e.g., such that the computing apparatus 12 may be configured to use information, or data, from the apparatus 20, 22, 24 and provide information, or data, to the apparatus 20, 22, 24). The input apparatus 20 may include any apparatus capable of providing input to the computing apparatus 12 to perform the functionality, methods, and/or logic described herein.

For example, the input apparatus 20 may include a touchscreen (e.g., capacitive touchscreen, a resistive touchscreen, a multi-touch touchscreen, etc.), a mouse, a keyboard, a trackball, etc. A touchscreen may overlay the display apparatus 22 such that, e.g., an operator may use the touchscreen to interact (e.g., by touch) with a graphical user interface displayed on the display apparatus 22. For example, the input apparatus 20 may allow an operator to interact with a graphical user interface including a configuration region for enabling or disabling PFR makeup processes and functionality as described herein when used in conjunction with the display apparatus 22 (e.g., displaying the graphical user interface).

The display apparatus 22 may include any apparatus capable of displaying information to an operator, such as a graphical user interface, etc., to perform the functionality, methods, and/or logic described herein. For example, the display apparatus 22 may include a liquid crystal display, an organic light-emitting diode screen, a touchscreen, a cathode ray tube display, etc. As described further herein, the display apparatus 22 may be configured to display a graphical user interface that includes one or more regions such as a configuration for configuring PFR makeup processes and functionality as well as various other regions and areas. For example, the graphical user interface displayed by the display apparatus 22 may include, or display, one or more fluid areas, each fluid area corresponding to a different fluid or a different pump used in an extracorporeal blood treatment. Further, each of these fluid areas may be used by an operator to adjust flow rates and view status information corresponding to a fluid such as flow rate, amount of fluid within a reservoir, an amount of time left before a reservoir change, etc.

The processing programs or routines 16 may include programs or routines for performing computational mathematics, matrix mathematics, standardization algorithms, comparison algorithms, or any other processing required to implement one or more exemplary methods and/or processes described herein. Data 18 may include, for example, PFR rate, PFR makeup volume, PFR makeup volume limits or maximums, patient weight data, reservoir mass data, pump data, pump stoppage data, alarm data, fluid data, other flow rates, fluid volumes, heuristics indicative of malfunction, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein, or any other data that may be necessary for carrying out the one and/or more processes or methods described herein.

In one or more embodiments, the system 10 may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The program used to implement the methods and/or processes described herein may be provided using any programmable language, e.g., a high-level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the system 10 may be implemented using a computer readable storage medium, configured with a computer program, where the storage medium so configured causes the computer to operate in a specific and predefined manner to perform functions described herein. Further, in at least one embodiment, the system 10 may be described as being implemented by logic (e.g., object code) encoded in one or more non-transitory media that includes code for execution and, when executed by a processor, is operable to perform operations such as the methods, processes, and/or functionality described herein.

The computing apparatus 12 may be, for example, any fixed or mobile computer system (e.g., a controller, a microcontroller, a personal computer, mini computer, etc.). The exact configuration of the computing apparatus 12 is not limiting, and essentially any device capable of providing suitable computing capabilities and control capabilities (e.g., pump flow rate control, PFR makeup calculation, control of extracorporeal blood treatment apparatus, etc.) may be used.

As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by computing apparatus 12 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by an operator.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

The methods and/or logic described in this disclosure, including those attributed to the systems, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described components may be implemented together or separately as discrete but interoperable logic devices. Depiction of different features, e.g., using block diagrams, etc., is intended to highlight different functional aspects and does not necessarily imply that such features must be realized by separate hardware or software components. Rather, functionality may be performed by separate hardware or software components or integrated within common or separate hardware or software components.

When implemented in software, the functionality ascribed to the systems, devices and methods described in this disclosure may be embodied as instructions and/or logic on a computer-readable medium such as RAM, ROM, NVRAM, EEPROM, FLASH memory, magnetic data storage media, optical data storage media, or the like. The instructions and/or logic may be executed by one or more processors to support one or more aspects of the functionality described in this disclosure.

The treatment apparatus 24 may include any apparatus used by an exemplary extracorporeal blood treatment system capable of performing extracorporeal blood treatments, such as, e.g., pumps, reservoirs, scales, treatment sets, filters, stoppages sensors, pressure sensors, etc. For example, the treatment apparatus 24 may include one or more elements, or components, of the extracorporeal blood treatment system 100 described herein with reference to FIG. 2.

The exemplary systems, and exemplary methods performed, or used, by such exemplary systems, described herein may be generally referred to as dialysis systems. The general term "dialysis" as used herein includes hemodialysis, hemofiltration, hemodiafiltration, hemoperfusion, liver dialysis, and therapeutic plasma exchange (TPE), among other similar treatment procedures. In dialysis generally, blood is taken out of the body and exposed to a treatment device to separate substances therefrom and/or to add substances thereto, and is then returned to the body. Although extracorporeal blood treatment systems capable of performing general dialysis (as defined above, including TPE) as well as those for infusion of drugs are to be contemplated herein, the illustrative systems may generally be configured to perform of continuous renal replacement therapy (CRRT). Additionally extracorporeal blood treatment systems that perform extracorporeal membrane oxygenation (ECMO), hemoperfusion, liver dialysis, apheresis, TPE, etc. may benefit from the systems, methods, and processes described herein and the present disclosure is not limited to any particular fluid processing system.

Figure 2:
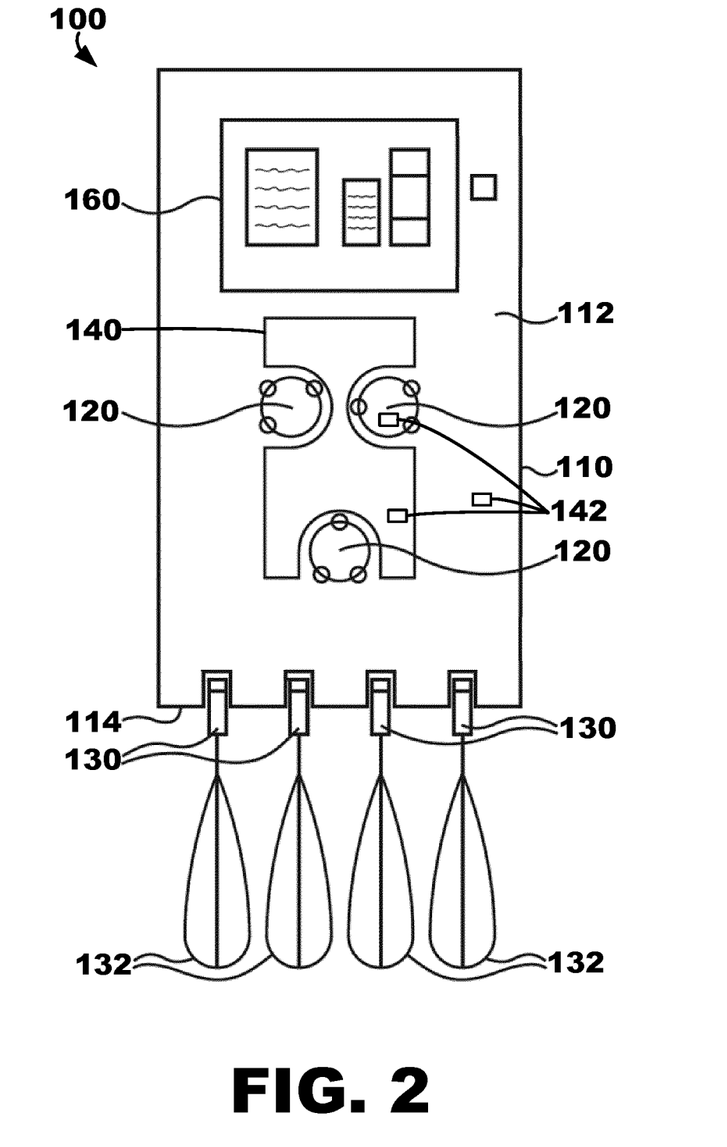
FIG. 2 is an illustration of an illustrative extracorporeal blood treatment system that may utilize the methods and processes described herein.

Referring to FIG. 2, one illustrative embodiment of an extracorporeal blood treatment system, or apparatus, 100 is depicted. The system 100 includes a housing 110 having a front face 112. The system 100 further includes one or more pumps 120, one or more disposable elements 140 (e.g., including or part of integrated modules), and one or more sensors 142 for use in performing one or more extracorporeal blood treatments. The one or more pumps 120 may be used to move liquids through the system as part of a treatment process. Although the pumps 120 are depicted in the form of peristaltic pumps, the pumps used in the extracorporeal blood treatment system described herein may be provided in a variety of alternative forms, e.g., piston pumps, pumps for use with syringes, diaphragm pumps, etc. The one or more pumps 120 may include one or more dialysate pumps and one or more effluent pumps. The dialysate pumps may be generally described as being on the upstream side of a blood treatment unit (e.g., a filter) on a dialysate circuit, and the effluent pumps may be generally described as being on the downstream side of the blood treatment unit on the dialysate circuit. The PFR rate may be the pump rate used by the one or more effluent pumps, which may be based on multiple inputs such as the dialysate pump rate, syringe pump rate, replacement pump rate, pre-blood pump rate.

The one or more disposable elements 140 may be coupled to the system 100 for using in performing the extracorporeal blood treatment. The one or more disposable elements 140 may include one or more fluid circuits such as, e.g., dialysis or dialysate fluid circuits, blood circuits, etc. and/or one or more blood treatment units such as, e.g., filters, etc. In at least one embodiment, a disposable element 140 is a cartridge or integrated unit including a plurality of various parts or portions configured to perform the extracorporeal blood treatment. Additionally, the one or more disposable elements 140 may include containers, or vessels, containing, or holding, one or more substances for use in the performance of the extracorporeal blood treatment. For example, a disposable element 140 may include a container, or vessel, holding bicarbonate, citrate, and/or dialysate/dialysis fluid, which may be operatively coupled to the dialysis/dialysate fluid circuit. Further, the disposable elements 140 may be described as providing at least a portion of the extracorporeal blood treatment fluid circuit that may be operatively coupled to one or more pumps 120 and one or more sensors 142 of the system 100 for use in performing extracorporeal blood treatments. As shown, two disposable elements 140 appear to be coupled to the front face 112 of the housing 110 of the system 100 to, e.g., integrate with the one or more other fluid circuits, pumps 120, and sensors 142 of the system 100.

As described herein, the one or more disposable elements 140 may be described as including one or more disposable fluid circuits and one or more blood treatment units operatively coupled to the one or more disposable fluid circuits. The one or more disposable elements 140 may be further described as including a blood circuit for receiving, circulating, and returning blood from/to a patient. The blood circuit may include one or more blood lines (e.g., as part of a disposable element). Further, the one or more disposable elements 140 may be further described as including a dialysis/dialysate circuit operatively coupled, or couplable, to the blood circuit to remove waste from the blood of the patient. The dialysis/dialysate circuit may receive, circulate, and return dialysis/dialysate fluid (e.g., returning dialysis/dialysate fluid including waste). The dialysis/dialysate circuit may include one or more dialysis/dialysate lines (e.g., as part of a disposable element 140). The blood treatment units may be, for example, a plasma filter, a hemodialysis filter, a hemofiltration filter, etc. Generally, the blood treatment units may be referred to as "filters."

As described herein, the system 100 may further include one or more sensors 142. As shown, three sensors 142 are identified on the system 100. One sensor 142 is located on, or coupled to, the front surface 112 of the housing 110, a second sensor 142 is located on, or coupled to, the disposable elements 140, and a third sensor 142 is located on, or coupled to, a pump 120. Additionally, the system 100 may include sensors 142 that are not visible on the outside of the housing 110, and instead, may be internal to the system 100 (e.g., within the housing 110). Generally, the system 100 may include any one or more sensors 142 so as to be able to monitor any value (e.g., any aspect, setting, level, condition, event internal to the system 100, etc.) of any process of the system 100 such as, e.g., processes during the performance of one or more extracorporeal blood treatments. For example, the system 100 may include one or more pressure sensors 142 operable to measure, or monitor, various pressures of various circuits, chambers, pods, reservoirs, etc. of the system 100, e.g., during the performance of an extracorporeal blood treatment, during the performance of a pre-treatment process, during the performance of a disinfection, post-treatment process, etc. Further, for example, the system 100 may include one or more flow rate sensors 142 operable to measure, or monitor, various fluid flow rates of fluids within various pumps, circuits, chambers, pods, reservoirs, etc. of the system 100, e.g., during the performance of an extracorporeal blood treatment, during the performance of a pre-treatment process, during the performance of a disinfection, post-treatment process, etc. Specifically, the system 100 may include one or more blood-related parameter sensors 142 such as, e.g., flow rate sensors to monitor various blood flow rates throughout the blood circuits of the system 100, blood pressure sensors to monitor the diastolic and systolic blood pressure of the patient, blood circuit pressure sensors to monitor the arterial and venous blood lines pressures, heart rate sensors to measure the patient's heart rate, etc. Further, for example, the system 100 may include one or more waste sensors 142 configured to, or operable, to measure, or monitor, an amount of waste being removing from a patient (e.g., from a patient's blood), e.g., during the performance of an extracorporeal blood treatment. Further, for example, the system 100 may include other sensors 142 such as fluid level sensors, temperature sensors, leak detection sensors, etc. that may be used before an extracorporeal blood treatment is performed, during the performance of an extracorporeal blood treatment, and/or after an extracorporeal blood treatment is performed.

Additionally, the extracorporeal blood treatment fluid circuit of the system 100 may be described as being completed by a combination of the disposable elements 140 and the system 100 and may be generally described as defining a blood circuit that removes blood from a patient, for example, via a catheter inserted in a vascular access of the patient, and takes the blood though a blood removal line. Then, the blood may pass through a chamber (e.g., a blood chamber) and, via a return line, may be transported back to the patient.

The extracorporeal blood treatment system 100 also includes, in one or more embodiments, a display 160 used to convey information to an operator or user. The display 160 may also serve as an input device if, e.g., the display 160 is in the form of a touchscreen. Also, although the display 160 is depicted as being located in the housing 110, in one or more alternate embodiments, the display 160 may be separate from the housing 110 of the extracorporeal blood treatment system 100. For example, the display 160 may be movably (e.g., swivel, tilt, etc.) attached, or coupled, to a top end of the housing 110.

The extracorporeal blood treatment system 100 also includes reservoir scales 130, which may be considered to be another type of sensor. Each of the reservoir scales 130 may configured to hold and weigh a reservoir 132. The reservoir scales 130 are positioned below a bottom end 114 of the housing 110, at least in part because the reservoirs 132 are typically attached to and hang from the reservoir scales 130. Although the depicted embodiment of extracorporeal blood treatment system 100 includes four reservoir scales 130 and associated reservoirs 132, alternative embodiments of an extracorporeal blood treatment apparatus as described herein may include one or more reservoir scales 130 and associated reservoirs 132 such as, e.g., as few as two reservoirs scales 130 and associated reservoirs 132, four or more reservoirs scales 130 and associated reservoirs 132, etc.

In the embodiment shown, the reservoirs 132 may be in the form of, e.g., flexible polymeric bags configured to hold liquids. Reservoirs 132, however, used in connection with the exemplary extracorporeal blood treatment systems described herein may take any suitable form in which liquids can be stored and weighed by any scale or weighing apparatus (e.g., such as reservoir scales 130), e.g., bottles, tanks, cartons, syringes, jugs, etc.

In one or more embodiments, the system 100 may provide an indication that a reservoir 132 attached to a reservoir scale 130 has passed a selected weight limit as a part of monitoring the status of the reservoirs. That selected weight limit may, in the case of a reservoir 132 used to collect liquids from the extracorporeal blood treatment apparatus, be an upper limit such that passing (e.g., reaching and/or exceeding) the selected weight limit is an indication that the reservoir 132 is reaching or has reached its loading capacity and may need to be replaced with a reservoir 132 having more capacity to collect liquid. In the case of a reservoir 132 used to supply liquids to the extracorporeal blood treatment apparatus, the selected weight limit may be a lower limit such that passing (e.g., reaching and/or falling below) the selected weight limit is an indication that the reservoir 132 is reaching or has reached a level at which the reservoir 132 may need to be replaced with a fresh reservoir 132 containing additional liquid to be supplied to the extracorporeal blood treatment system 100.

As shown in FIG. 1 and as related to FIG. 2, the treatment apparatus 24 may be operatively coupled, or connected, to the computing apparatus 12. Among the treatment apparatus 24 operably coupled to the computing apparatus 12 are the pumps 120 and reservoir scales 130 as shown in FIG. 2.

The computing apparatus 12 may, in one or more embodiments, be configured to receive a weight signal from each reservoir scale 130, with the weight signal from each reservoir scale 130 being indicative of the weight of a reservoir 132 attached to the reservoir scale 130. The computing apparatus 12 may further be configured to make one or more flow rate adjustments, or determination, based the weight signal that has been received from the reservoir scales 130. For example, the reservoir scales 130 may be used to determine how much fluid has been removed from a patient (PFR), and the system 100, for example, may use this information to determine the speed of one or more pumps such as, e.g., dialysate pumps, effluent pumps, pre-blood pumps, and replacement pumps.

The reservoir scales used to hold and weigh reservoirs used in the extracorporeal blood treatment apparatus described herein may take any number of a variety of different forms. Examples of some potentially suitable reservoir scales and associated structure may be found in International Publication WO 2004/069311 and U.S. Pat. No. 7,891,625, as well as the reservoir scales and hangers used in some commercially available hemodialysis machines (e.g., PRISMAFLEX machines available from Gambro Lundia AB, etc.).

Figure 3:
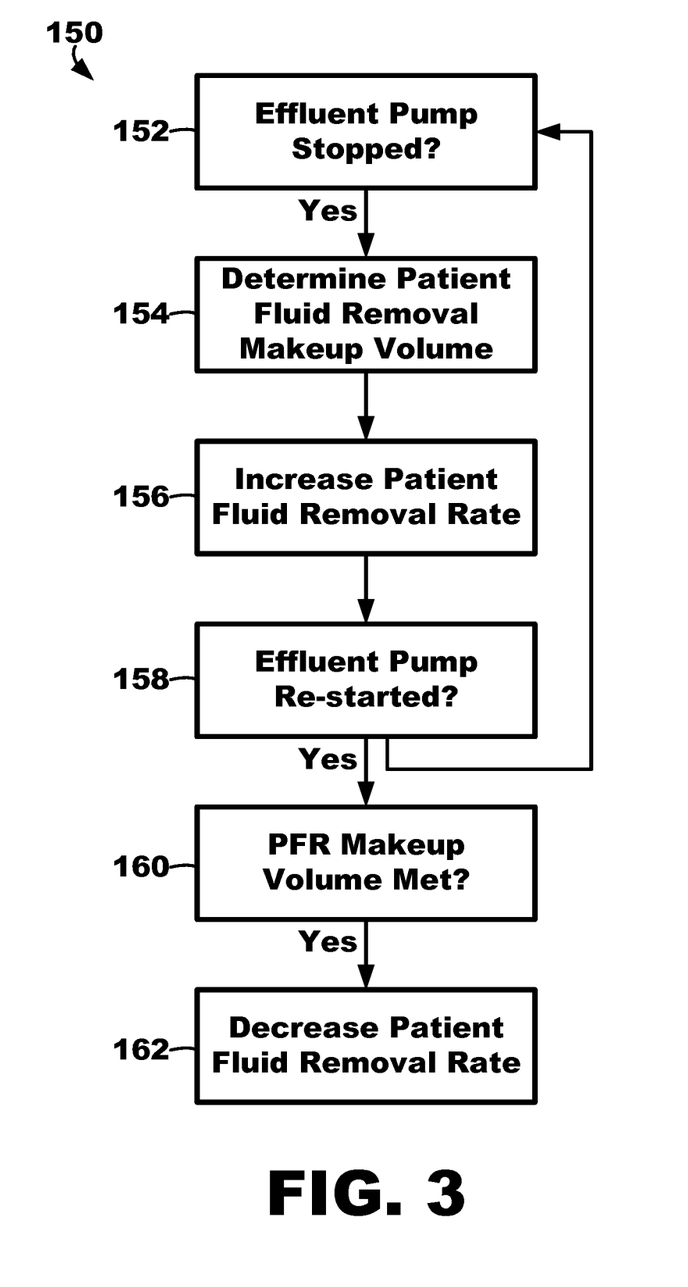
FIG. 3 is a flow diagram of an illustrative method of patient fluid removal makeup for use in extracorporeal blood treatment systems, e.g., such as shown generally in FIGS. 1-2.

An illustrative method 150 of patient fluid removal (PFR) makeup for extracorporeal blood treatments is depicted in FIG. 3. The illustrative method of PFR makeup may be used, or executed by, one or both of the system 10 described herein with reference to FIG. 1 and the system 100 of FIG. 2.

The method 150 may include determining whether the pump has stopped 152. In particular, determining whether the pump has stopped 152 may include determining whether the effluent pump (e.g., located downstream from the blood treatment unit (e.g., filter)) has been stopped. Generally, the effluent pump and the dialysate pump (e.g., located upstream from the blood treatment unit (e.g., filter)) of the dialysate circuit may be stopped at the same time. In other words, when the effluent pump is stopped, the dialysate pump is also stopped, and conversely, when the dialysate pump is stopped, the effluent pump is also stopped.

The effluent pump (and the dialysate pump) may be stopped for many reasons. Some of the reasons for stoppage may be user-initiated and other reasons for stoppage may be system-initiated or automatic. An example of a user-initiated stoppage may be a user selecting (e.g., touching, clicking on, etc.) a stop, or pause, graphical region of the graphical user interface, which may stop the ongoing extracorporeal blood treatment. After resolving whatever issue prompted the user to select the stop the ongoing extracorporeal blood treatment, the user may re-start the extracorporeal blood treatment. An example of a system-initiated stoppage may be an alarm condition where a stoppage is required such as, e.g., a dialysate circuit leak, excessive pressure due to clamped blood line or clotted catheter, excessive pressure due to clogged filter, weight scale disturbances, return line air bubble detection, weight errors due to clamped or unconnected fluid lines, etc. After resolving the alarm condition, a user may re-start the extracorporeal blood treatment.

Other stoppage reasons may include a reservoir, or bag, change. For example, an effluent bag for receiving effluent may become full over the course of an extracorporeal blood treatment, and thus may need be replaced. During the replacement of the effluent bag, the dialysate circuit may be stopped, and thus, the effluent pump and the dialysate pump may be stopped. Other reservoir changes may also result in stoppage. It is to be understood that there many reasons for stoppage of the dialysate circuit, and in particular, the effluent pump, and the illustrative systems and methods described herein are intended to be utilized with any sort of stoppage that results in stoppage of patient fluid removal (PFR).

During a stoppage of the dialysate circuit or effluent pump, fluid will not be removed from the patient over the course of the stoppage time. To keep track of the "lost" PFR, the illustrative method 150 may utilize, or use, a patient fluid removal (PFR) makeup volume. More specifically, the illustrative method 150 may determine a PFR makeup volume 154 in response to stoppage of the effluent pump (and remainder of the dialysate circuit). The PFR makeup volume may be described as a volume of fluid removal from the patient that did not occur during the stoppage.

In one embodiment, determining the PFR makeup volume 154 may include increasing the PFR makeup volume as time elapses during the stoppage. In other words, the method 150 may increase the PFR makeup volume in response to stoppage of an effluent pump. More specifically, the PFR makeup volume may be increased by the amount of fluid removal from the patient that should occur over the stoppage time. This amount of fluid removal may be determined, or calculated, using the patient fluid removal (PFR) rate and the elapsed stoppage time. The PFR makeup volume may be incremented over time according to the PFR rate until the stoppage ends. In another embodiment, the PFR makeup volume may be calculated when the stoppage ends by multiplying the PFR rate and the elapsed stoppage time.

Additionally, it is to be understood that the present stoppage may not be the first stoppage during an extracorporeal blood treatment. Thus, if the PFR makeup volume was already greater than zero when the present stoppage occurred, the presently determined PFR makeup volume will be added to the previous non-zero PFR makeup volume. If using the incremental process, the previous PFR makeup volume may simply be increased during stoppage time. If using the calculated-when-stoppage-ends process, the new PFR makeup volume may be added to the previous PFR makeup volume.

Nonetheless, the process 154 of method 150 may result in a PFR makeup volume that may be used to "make up" the fluid removal that did not occur during the stoppage when the effluent pump, and dialysis circuit, re-start.

Additionally, in one or more embodiments, the amount of PFR makeup volume may be limited to a selected amount. In other words, the PFR makeup volume may have a maximum amount that the illustrative systems and methods allow it to be. In at least one embodiment, the PFR makeup volume may be limited to less than or equal to a PFR makeup volume limit. The PFR makeup volume limited may be a selected value (e.g., selected by a user, selected by a clinic administrator, etc.), a fixed value (e.g., programmed by the manufacturer or distributor), and a determined, or computed, value that is determined based on one or more factors (e.g., patient weight, patient age, treatment type, etc.). In at least one embodiment, the PFR makeup volume limit may be equal to the present PFR rate (e.g., prior to an increase via the method 150) multiplied by, or times, a selected period of time such as, e.g., 10 minutes.

In one or more embodiments, it may be described that the PFR volume prescribed is a time integral of operator entered PFR rate. The PFR volume will continue to increase as long as treatment is active even if the fluid pumps are stopped due to a bag change of alarm as long as the PFR volume limit has not been reached. The actual PFR volume commanded is the time integral the commanded effluent flow rate minus the estimated syringe flow rate minus the replacement, dialysate, and pre-blood pump (PBP) flow rates. The commanded flow rates are all zero when the fluid pumps are stopped for a bag change or alarm. Thus, the PFR volume commanded is static when the fluid pumps are stopped. The PFR makeup volume may then be the PFR volume prescribed minus the PFR volume commanded. This is not dependent on the measured PFR as it is left to the individual closed loop pump weight controllers to achieve the commanded flow rate for each individual fluid bag.

The illustrative method 150 may further include increasing the PFR rate in response to stoppage of the effluent pump (and remainder of the dialysate circuit) 156. The increased PFR rate may be used after the stoppage ceases when the effluent pump (as well as dialysate pump) re-start to, e.g., make up for the lost PFR during the stoppage.

In one or more embodiments, the increase to the PFR rate may be referred to as a PFR makeup rate, which may be based on the PFR volume prescribed (e.g., a time integral of prescribed PFR) compared to actual PFR volume commanded. It is to be understood that there is no dependence on the actual measured PFR volume. In other words, the determination to increase the PFR, or the PFR makeup rate, may not be dependent on the weight (or volume computed from the weight) of the fluid that is actually removed from the patient, and instead, is based on the prescribed PFR rate and the time of the stoppage (to, e.g., compute a PFR makeup volume).

The PFR rate may be increased in many different ways. In one example, the PFR rate may be increased by a selected percentage. The selected percentage may be greater than or equal to about 2.5%, greater than or equal to about 7.5%, greater than or equal to about 12.5%, greater than or equal to about 17.5%, etc. Further, the selected percentage may be less than or equal to about 30%, less than or equal to about 25%, less than or equal to about 22.5%, less than or equal to about 15%, etc. In at least one embodiment, the selected percentage is 20%. In this example, if the PFR rate was originally prescribed and configured to be 80 milliliters (ml) per hour, the increased PFR rate may be 96 ml per hour.

In another example, the PFR rate may be increased by a selected rate of fluid removal related to mass of the patient. The selected rate of fluid removal may be greater than or equal to about 0.5 ml per hour per kilogram, greater than or equal to about 1 ml per hour per kilogram., greater than or equal to about 1.75 ml per hour per kilogram, etc. Further, the selected rate of fluid removal may be less than or equal to about 1.5 nil per hour per kilogram, less than or equal to about 2.5 ml per hour per kilogram, less than or equal to about 3.5 ml per hour per kilogram, etc. In at least one embodiment, the selected rate of fluid removal is 2 ml per hour per kilogram. In this example, if the PFR rate was originally prescribed and configured to 80 milliliters (ml) per hour and the patient weighs 5 kilograms, the PFR rate may be determined to be 90 ml per hour.

The selected percentage PFR rate increase process and the selected rate of fluid removal related to mass of the patient PFR rate increase process may also be used in conjunction, and the lesser of the two values may be used. This determination to use the lesser of the two values generated from the selected percentage PFR rate increase process and the selected rate of fluid removal related to mass of the patient PFR rate increase process may provide additional follow-up on the PFR rate when high PFR rates are used on small patients due to nurses compensating for additional infusion of fluids.

Still further, the PFR rate increase may be further limited by other selected limits and other factors. For example, PFR Rate increase may be reduced due to low blood flow rate. For instance the total PFR rate including the increase due to PFR makeup may be limited to abut 50% of the blood flow rate. Further, in one or more embodiments, the PFR rate operator entry in the monitor prescription entry on the graphical user interface is limited to a maximum of 50% of the patient blood flow rate. The constraint on the increase on PFR (e.g., PFR makeup rate) means that as the prescribed PFR rate approaches the 50% limit, the maximum increase to PFR (e.g., maximum PFR makeup rate) may be reduced or even limited to zero rate, if the prescribed PFR rate is already at the limit.

Additionally, although it described herein that the PFR rate is increased in response to stoppage of the effluent pump, in one or more embodiments, the PFR rate may be increased based on the PFR makeup volume. For example, if the PFR makeup volume is greater than zero, then the PFR rate may be increased.

As shown, the method 150 may further include re-starting the effluent pump 158. Once the effluent pump is re-started, the increased PFR rate may be used until the PFR makeup volume is met, or compensated for, 160, and then, the PFR rate may be decreased 162. For example, the method 150 may continue providing an extracorporeal blood treatment after the effluent pump is re-started using the increased PFR rate (e.g., the original PFR rate plus a PFR makeup rate) until an amount, or volume, of fluid beyond what is being prescribed that is removed from the patient equals the PFR makeup volume. In other words, the increased PFR rate may be used until the PFR makeup volume is "made up," then the PFR rate may decreased to, e.g., the value prior to the increase, the prescribed value, etc.

The PFR makeup volume may be adjusted in response to the increased PFR rate after the effluent pump is re-started in many different ways. For example, the PFR makeup value decremented, or decreased, in real time, or the PFR makeup value decreased upon the occurrence of an event.

More specifically, in one or more embodiments, the PFR makeup volume may be decremented over time as additional fluid is removed from the patient. In this way, if another stoppage occurs, the PFR makeup volume will be "current" such that, e.g., it may be increased during the new stoppage with conducting any further processing.

Further, more specifically, in one or more embodiments, the PFR makeup volume may adjusted either when the amount of fluid additionally removed from the patient meets the PFR makeup volume or when another stoppage occurs.

In the case the amount of fluid additionally removed from the patient meeting, or equaling, the PFR makeup volume, the PFR makeup volume may be set back, or programmed, to zero. In the case of stoppage, the amount of fluid additionally removed from the patient may be subtracted from the PFR makeup volume to make the PFR makeup volume "current" such that, e.g., it may be increased during the new stoppage.

Additionally, after the effluent pump (and the remainder of the dialysate circuit) is re-started, the method 150 may continue to monitor for another effluent pump stoppage as indicated on the flow chart of FIG. 3 by the arrow looping from process 158 back to process 152.

Figure 4:
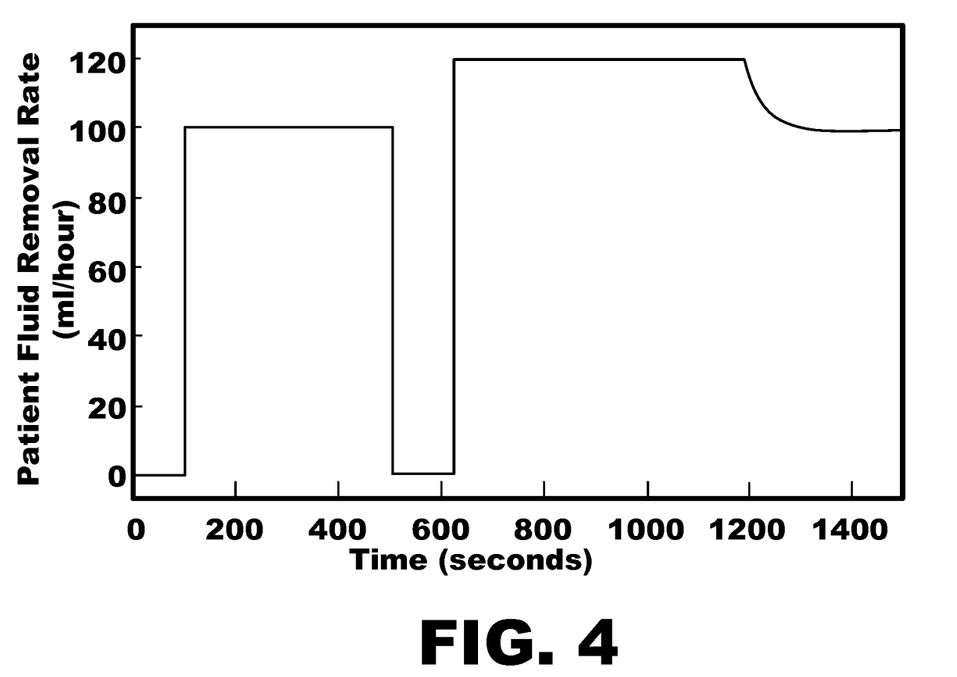
FIGS. 4-7 depict various graphs of an example of patient fluid removal makeup for use in extracorporeal blood treatment systems and methods, e.g., such as shown generally in FIGS. 1-3.

An example of PFR makeup for use in illustrative extracorporeal blood treatment systems and methods is shown, or depicted, in various graphs in FIGS. 4-7. PFR rate over time during an extracorporeal blood treatment is depicted in FIG. 4. As shown, the PFR rate starts as 100 ml/hour but is decreased to 0 ml/hour at 500 seconds. The PFR rate of 0 ml/hour indicates a stoppage. As shown, the stoppage occurs from 500 seconds to 620 seconds.

Figure 5:
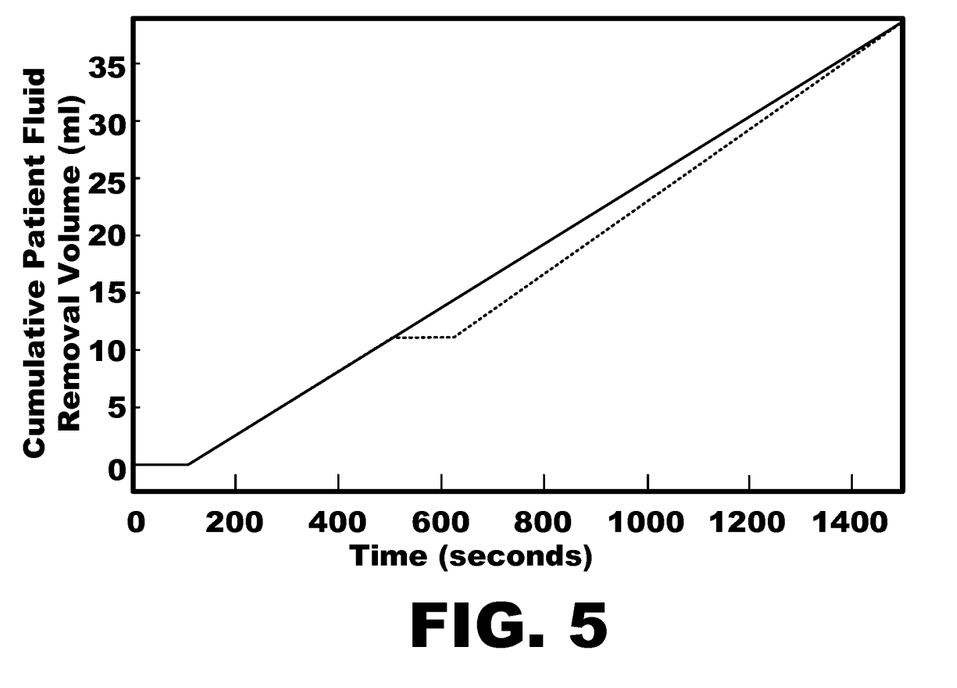

During the stoppage, the prescribed cumulative PFR will not be met as shown in the graph of FIG. 5, which shows the prescribed cumulative PFR (solid line) and the actual commanded cumulative PFR (dotted line) over time. As shown, when the stoppage occurs from 500 seconds to 620 seconds, the actual commanded cumulative PFR flat-lines while the prescribed cumulative PFR continues to grow.

Figure 6:
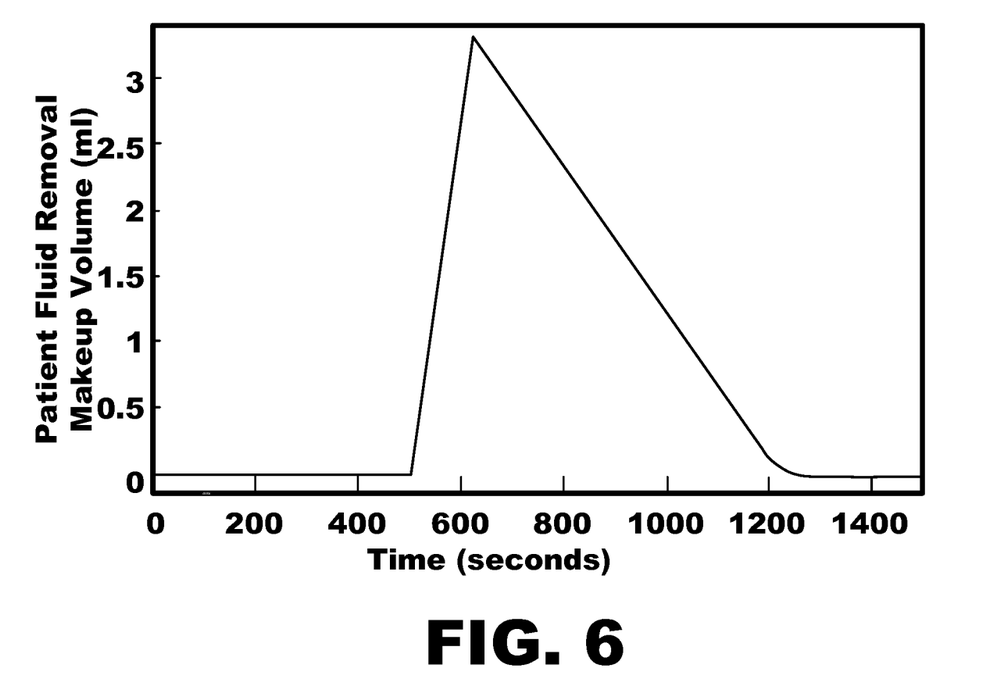

To compensate for the "lost" PFR, the illustrative systems and methods may determine a PFR makeup volume and increase the PFR rate following re-starting the effluent pump. PFR makeup volume over time is depicted in FIG. 6. As shown, when the stoppage begins at 500 seconds, the PFR makeup volume starts to increase, and ceases to increase at 620 seconds when the effluent pump is restarted. The PFR makeup volume is about 3.4 ml when the effluent pump is restarted.

Figure 7:
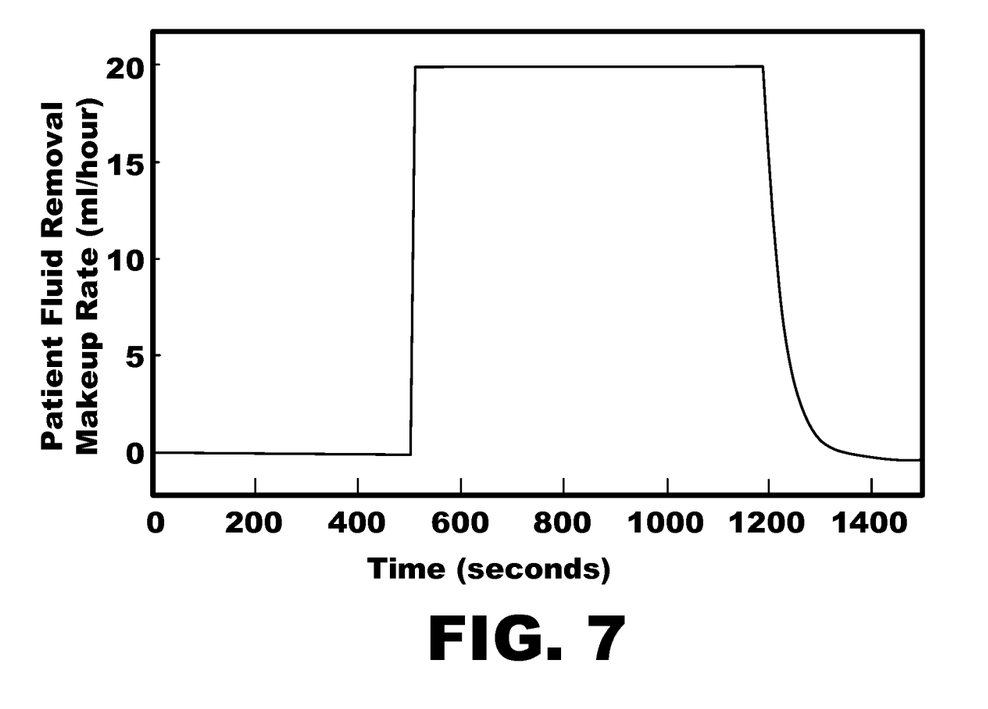

A PFR makeup rate over time is depicted in FIG. 7. The PFR makeup rate may represent the increase to the PFR rate to compensate for the lost PFR during stoppage. In this example, when the stoppage occurs at 500 seconds, the PFR makeup rate increased from 0 ml/hr to 20 ml/hr, which is 20% of the original PFR rate. Thus, the PFR rate as depicted in FIG. 4 may be increased by the PFR makeup rate, which in this example is 20 ml/hr, when the stoppage ceases at 620 seconds. As shown in FIG. 4, at 620 seconds, the PFR rate is increased to 120 ml/hr.

After the commanded PFR rate is increased after the stoppage, the PFR makeup volume as shown in FIG. 6 may begin to decrease, and continues to decrease until the PFR makeup volume approaches zero. At about 1200 seconds, the PFR makeup volume is approaching 0 ml, and thus, the PFR makeup rate may no longer be needed and may be decreased as shown in FIG. 7, which therefore decreases the PFR as shown in FIG. 4. As shown in FIG. 5, the actual commanded PFR approaches the prescribed PFR at about 1400 seconds. In this way, the increased PFR has effectively "made up" the lost PFR.

In other words, FIGS. 4-7 depict an example test case on an illustrative system utilizing a PFR prescription rate set to 100 ml/hour. In this case, the fluid pumps were stopped for 120 seconds (from 500 seconds to 620 seconds on the plot). The plots show the resulting PFR makeup volume and subsequent increases in the effluent pump speed to compensate for the PFR volume deficit while the pumps were paused.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the systems and methods described herein. Various modifications of the illustrative embodiments, as well as additional embodiments of the disclosure, will be apparent upon reference to this description.

What is claimed:

1. An extracorporeal blood treatment system comprising:
   extracorporeal blood treatment apparatus comprising one or more pumps and one or more sensors for use in performing an extracorporeal blood treatment, wherein the one or more pumps comprise an effluent pump to remove fluid from a patient during extracorporeal blood treatment according to a patient fluid removal rate; and
   a computing apparatus comprising one or more processors and operatively coupled to the extracorporeal blood treatment apparatus, wherein the computing apparatus is configured to:
      run the effluent pump to remove fluid from the patient based on the patient fluid removal rate during an extracorporeal blood treatment;
      stop the effluent pump;
      determine a patient fluid removal makeup volume in response to the stoppage of the effluent pump, wherein the patient fluid removal makeup volume is a volume of patient fluid that was not removed during the stoppage; and
      increase the patient fluid removal rate in response to the stoppage of the effluent pump and the determination of the patient fluid removal makeup volume for use after the stoppage ceases, wherein increasing the patient fluid removal rate comprises increasing the patient fluid removal rate by a selected rate of fluid removal; and
      re-start the effluent pump to run based on the increased patient fluid removal rate.

2. The system as set forth in claim 1, wherein the computing apparatus is further configured to limit the patient fluid removal makeup volume to less than or equal to a patient fluid removal makeup volume limit.

3. The system as set forth in claim 2, wherein the patient fluid removal makeup volume limit equals a patient fluid removal rate multiplied by a selected period of time.

4. The system as set forth in claim 3, wherein the patient fluid removal makeup volume limit equals a current patient fluid removal rate setting multiplied by 10 minutes.

5. The system as set forth in claim 2, wherein the computing apparatus is further configured to recalculate the patient fluid removal makeup volume limit in response to a change of a patient fluid removal rate setting.

6. The system as set forth in claim 2, wherein the patient fluid removal makeup volume limit is reduced down to zero in response to a patient fluid removal rate setting being set to zero.

7. The system as set forth in claim 1, wherein the selected rate of fluid removal is less than or equal to 3.5 milliliters per hour per kilogram and is greater than or equal to 1 milliliter per hour per kilogram.

8. The system as set forth in claim 1, wherein the selected rate of fluid removal comprises one or more of:

a selected percentage patient fluid removal rate increase; and a selected rate of fluid removal related to mass of the patient fluid removal rate increase.

9. The system as set forth in claim 1, wherein increasing the patient fluid removal rate comprises limiting the patient fluid removal rate based on a blood flow rate.

10. The system as set forth in claim 1, wherein the increased patient fluid removal rate is limited to 50% of a blood flow rate.

11. The system as set forth in claim 1, wherein the stoppage of the effluent pump comprises one or more of a bag change, an alarm condition, and a user-initiated action.

12. The system as set forth in claim 1, wherein the computing apparatus is further configured to decrease the patient fluid removal makeup volume in response to continuation of the effluent pump when using the increased patient fluid removal rate.

13. The system as set forth in claim 1, wherein the computing apparatus is further configured to decrease the patient fluid removal rate in response to an additional volume of fluid removed from the patient being equal to the patient fluid removal makeup volume, wherein decreasing the patient fluid removal rate comprises returning the patient fluid removal rate to a value of the patient removal rate prior to the increase thereto.

14. The system as set forth in claim 1, wherein the computing apparatus is further configured to allow a user to select whether to enable the patient fluid removal makeup volume is increasable.

15. The system as set forth in claim 1, wherein a patient fluid removal volume prescribed is a time integral of an operator entered patient fluid removal rate, the patient fluid removal volume prescribed continuing to increase as long as treatment is active, even if fluid pumps are stopped due to a bag change or alarm as long as a patient fluid removal volume limit has not been reached.

16. The system as set forth in claim 15, wherein a patient fluid removal volume commanded is the time integral of a commanded effluent flow rate minus a syringe flow rate, minus a replacement flow rate, minus a dialysate flow rate, and minus a pre-blood pump flow rate.

17. The system as set forth in claim 16, wherein the patient fluid removal makeup volume is the patient fluid removal volume prescribed minus the patient fluid removal volume commanded.

18. An extracorporeal blood treatment system comprising:
extracorporeal blood treatment apparatus comprising one or more pumps and one or more sensors for use in performing an extracorporeal blood treatment, wherein the one or more pumps comprise an effluent pump to remove fluid from a patient during extracorporeal blood treatment according to a patient fluid removal rate; and
a computing apparatus comprising one or more processors and operatively coupled to the extracorporeal blood treatment apparatus, wherein the computing apparatus is configured to:
run the effluent pump to remove fluid from the patient based on the patient fluid removal rate during an extracorporeal blood treatment;
stop the effluent pump;
determine a patient fluid removal makeup volume in response to the stoppage of the effluent pump, wherein the patient fluid removal makeup volume is a volume of patient fluid that was not removed during the stoppage;
increase the patient fluid removal rate in response to the stoppage of the effluent pump and the determination of the patient fluid removal makeup volume for use after the stoppage ceases, wherein increasing the patient fluid removal rate comprises increasing the patient fluid removal rate by a selected percentage in response to an increased patient fluid removal makeup volume, and wherein the selected percentage is less than or equal to 30% and greater than or equal to 7.5%; and
re-start the effluent pump to run based on the increased patient fluid removal rate.

19. The system as set forth in claim 18, wherein the computing apparatus is further configured to limit the patient fluid removal makeup volume to less than or equal to a patient fluid removal makeup volume limit, wherein the patient fluid removal makeup volume limit equals the patient fluid removal rate multiplied by a selected period of time.

20. The system as set forth in claim 18, wherein increasing the patient fluid removal rate comprises limiting the patient fluid removal rate based on a blood flow rate.

21. The system as set forth in claim 18, wherein the increased patient fluid removal rate is limited to 50% of a blood flow rate.

22. An extracorporeal blood treatment system comprising:
extracorporeal blood treatment apparatus comprising one or more pumps and one or more sensors for use in performing an extracorporeal blood treatment, wherein the one or more pumps comprise an effluent pump to remove fluid from a patient during extracorporeal blood treatment according to a patient fluid removal rate; and
a computing apparatus comprising one or more processors and operatively coupled to the extracorporeal blood treatment apparatus, wherein the computing apparatus is configured to:
run the effluent pump to remove fluid from the patient based on the patient fluid removal rate during an extracorporeal blood treatment;
stop the effluent pump;
determine a patient fluid removal makeup volume in response to the stoppage of the effluent pump, wherein the patient fluid removal makeup volume is a volume of patient fluid that was not removed during the stoppage;
increase the patient fluid removal rate in response to the stoppage of the effluent pump and the determination of the patient fluid removal makeup volume for use after the stoppage ceases, wherein increasing the patient fluid removal rate comprises using a patient fluid removal rate value, wherein the patient fluid removal rate value comprises one or more of:
a selected percentage patient fluid removal rate increase;
a selected rate of fluid removal related to mass of the patient fluid removal rate increase; and
a rate based on blood flow rate,
wherein the increased patient fluid removal rate is limited to 50% of the blood flow rate; and
re-start the effluent pump to run based on the increased patient fluid removal rate.

23. The system as set forth in claim 22, wherein the patient fluid removal makeup volume is an additional effluent volume calculated to compensate for the patient fluid removal volume not removed when treatment is stopped due to an alarm or fluid bag change, wherein a patient fluid removal volume prescribed is a time integral of an operator entered patient fluid removal rate, wherein the patient fluid removal volume prescribed continues to increase as long as treatment is active, even if fluid pumps are stopped due to a bag change or alarm as long as a patient fluid removal volume limit has not been reached, wherein a patient fluid removal volume commanded is the time integral of a commanded effluent flow rate minus a syringe flow rate, minus a replacement flow rate, minus a dialysate flow rate, and minus a pre- blood pump flow rate, and wherein the patient fluid removal makeup volume is the patient fluid removal volume prescribed minus the patient fluid removal volume commanded.

24. An extracorporeal blood treatment system comprising:
extracorporeal blood treatment apparatus comprising one or more pumps and one or more sensors for use in performing an extracorporeal blood treatment, wherein the one or more pumps comprise an effluent pump to remove fluid from a patient during extracorporeal blood treatment according to a patient fluid removal rate; and
a computing apparatus comprising one or more processors and operatively coupled to the extracorporeal blood treatment apparatus, wherein the computing apparatus is configured to:
run the effluent pump to remove fluid from the patient based on the patient fluid removal rate during an extracorporeal blood treatment;
stop the effluent pump;
determine a patient fluid removal makeup volume in response to the stoppage of the effluent pump, wherein the patient fluid removal makeup volume is a volume of patient fluid that was not removed during the stoppage;
increase the patient fluid removal rate in response to the stoppage of the effluent pump and the determination of the patient fluid removal makeup volume for use after the stoppage ceases, wherein increasing the patient fluid removal rate comprises increasing the patient fluid removal rate by a selected rate of fluid removal related to mass of the patient in response to the determined patient fluid removal makeup volume, wherein the selected rate of fluid removal is less than or equal to 3.5 milliliters per hour per kilogram and is greater than or equal to 1 milliliter per hour per kilogram; and
re-start the effluent pump to run based on the increased patient fluid removal rate.

25. The system as set forth in claim 24, wherein the computing apparatus is further configured to decrease the patient fluid removal makeup volume in response to continuation of the effluent pump when using the increased patient fluid removal rate.

26. The system as set forth in claim 24, wherein the patient fluid removal makeup volume is a patient fluid removal volume prescribed minus a patient fluid removal volume commanded.

27. The system as set forth in claim 24, wherein the patient fluid removal makeup volume is an additional effluent flow volume calculated to compensate for a patient fluid removal volume not removed when treatment is stopped due to an alarm or fluid bag change.

28. The system as set forth in claim 24, wherein the computing apparatus is further configured to limit the patient fluid removal makeup volume to less than or equal to a patient fluid removal makeup volume limit.

29. An extracorporeal blood treatment system comprising:
extracorporeal blood treatment apparatus comprising one or more pumps and one or more sensors for use in performing an extracorporeal blood treatment, wherein the one or more pumps comprise an effluent pump to remove fluid from a patient during extracorporeal blood treatment according to a patient fluid removal rate; and
a computing apparatus comprising one or more processors and operatively coupled to the extracorporeal blood treatment apparatus, wherein the computing apparatus is configured to:
run the effluent pump to remove fluid from the patient based on the patient fluid removal rate during an extracorporeal blood treatment;
stop the effluent pump;
determine a patient fluid removal makeup volume in response to the stoppage of the effluent pump, wherein the patient fluid removal makeup volume is a volume of patient fluid that was not removed during the stoppage;
increase the patient fluid removal rate in response to the stoppage of the effluent pump and the determination of the patient fluid removal makeup volume for use after the stoppage ceases, wherein increasing the patient fluid removal rate comprises increasing the patient fluid removal rate by a selected rate of fluid removal, wherein the selected rate of fluid removal comprises one or more:
a selected percentage patient fluid removal rate increase; and
a selected rate of fluid removal related to mass of the patient fluid removal rate increase; and
re-start the effluent pump to run based on the increased patient fluid removal makeup volume.

30. The system as set forth in claim 29, wherein the patient fluid removal makeup volume is a patient fluid removal volume prescribed minus a patient fluid removal volume commanded.

31. The system as set forth in claim 29, wherein the patient fluid removal makeup volume is an additional effluent volume calculated to compensate for the patient fluid removal volume not removed when treatment is stopped due to an alarm or fluid bag change.

32. The system as set forth in claim 29, wherein the computing apparatus is further configured to limit the patient fluid removal makeup volume to less than or equal to a patient fluid removal makeup volume limit.

33. An extracorporeal blood treatment system comprising:
extracorporeal blood treatment apparatus comprising one or more pumps and one or more sensors for use in performing an extracorporeal blood treatment, wherein the one or more pumps comprise an effluent pump to remove fluid from a patient during extracorporeal blood treatment according to a patient fluid removal rate; and
a computing apparatus comprising one or more processors and operatively coupled to the extracorporeal blood treatment apparatus, wherein the computing apparatus is configured to:
run the effluent pump to remove fluid from the patient based on the patient fluid removal rate during an extracorporeal blood treatment;
stop the effluent pump;
determine a patient fluid removal makeup volume in response to the stoppage of the effluent pump, wherein the patient fluid removal makeup volume is a volume of patient fluid that was not removed during the stoppage;
increase the patient fluid removal rate in response to the stoppage of the effluent pump and the determination of the patient fluid removal makeup volume for use after the stoppage ceases, wherein increasing the patient fluid removal rate comprises increasing the patient fluid removal rate by a selected rate of fluid removal related to mass of the patient in response to an increased patient fluid removal makeup volume;

re-start the effluent pump to run based on the increased patient fluid removal rate;

decrease the patient fluid removal makeup volume in response to continuation of the effluent pump when using the increased patient fluid removal rate.

34. The system as set forth in claim 33, wherein the patient fluid removal makeup volume is a patient fluid removal volume prescribed minus a patient fluid removal volume commanded.

35. The system as set forth in claim 33, wherein the patient fluid removal makeup volume is an additional effluent volume calculated to compensate for a patient fluid removal volume not removed when treatment is stopped due to an alarm or fluid bag change.

36. An extracorporeal blood treatment system comprising:

extracorporeal blood treatment apparatus comprising one or more pumps and one or more sensors for use in performing an extracorporeal blood treatment, wherein the one or more pumps comprise an effluent pump to remove fluid from a patient during extracorporeal blood treatment according to a patient fluid removal rate; and a computing apparatus comprising one or more processors and operatively coupled to the extracorporeal blood treatment apparatus, wherein the computing apparatus is configured to:

run the effluent pump to remove fluid from the patient based on the patient fluid removal rate during an extracorporeal blood treatment;

stop the effluent pump;

determine a patient fluid removal makeup volume in response to the stoppage of the effluent pump, wherein the patient fluid removal makeup volume is a volume of patient fluid that was not removed during the stoppage;

increase the patient fluid removal rate in response to the stoppage of the effluent pump and the determination of the patient fluid removal makeup volume for use after the stoppage ceases, wherein increasing the patient fluid removal rate comprises increasing the patient fluid removal rate by a selected rate of fluid removal related to mass of the patient in response to an increased patient fluid removal makeup volume;

re-start the effluent pump to run based on the increased patient fluid removal rate; and decrease the patient fluid removal rate in response to an additional volume of fluid removed from the patient being equal to the patient fluid removal makeup volume, wherein decreasing the patient fluid removal rate comprises returning the patient fluid removal rate to a value of the patient removal rate prior to the increase thereto.

37. The system as set forth in claim 36, wherein the patient fluid removal makeup volume is a patient fluid removal volume prescribed minus a patient fluid removal volume commanded.

38. The system as set forth in claim 36, wherein the patient fluid removal makeup volume is an additional effluent volume calculated to compensate for the patient fluid removal volume not removed when treatment is stopped due to an alarm or fluid bag change.

39. The system as set forth in claim 36, wherein the computing apparatus is further configured to limit the patient fluid removal makeup volume to less than or equal to a patient fluid removal makeup volume limit.

* * * * *